United States Patent
Kim et al.

(10) Patent No.: US 9,759,539 B2
(45) Date of Patent: Sep. 12, 2017

(54) METHOD OF MOTION TRACKING

(75) Inventors: Jinwook Kim, Seoul (KR); Yujin Jung, Seoul (KR); Donghoon Kang, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 655 days.

(21) Appl. No.: 14/119,960

(22) PCT Filed: Feb. 15, 2012

(86) PCT No.: PCT/KR2012/001119
§ 371 (c)(1),
(2), (4) Date: Jan. 30, 2014

(87) PCT Pub. No.: WO2012/161407
PCT Pub. Date: Nov. 29, 2012

(65) Prior Publication Data
US 2014/0156218 A1  Jun. 5, 2014

(30) Foreign Application Priority Data
May 25, 2011  (KR) .................. 10-2011-0049804

(51) Int. Cl.
*G06F 3/01* (2006.01)
*G01B 5/004* (2006.01)
(Continued)

(52) U.S. Cl.
CPC ............ *G01B 5/004* (2013.01); *A61B 5/1114* (2013.01); *G06F 3/011* (2013.01); *A61B 5/6822* (2013.01);
(Continued)

(58) Field of Classification Search
CPC ... G01B 5/004; A61B 5/1114; A61B 2503/10; A61B 5/6823; A61B 5/6813; A61B 5/6824; G06F 3/011
See application file for complete search history.

(56) References Cited

U.S. PATENT DOCUMENTS

| 7,089,148 B1 | 8/2006 | Bachmann et al. |
| 2008/0285805 A1* | 11/2008 | Luinge .................... G06F 3/011 |
| | | 382/107 |
| 2009/0322763 A1* | 12/2009 | Bang ................... G06K 9/00342 |
| | | 345/474 |

FOREIGN PATENT DOCUMENTS

| KR | 10-2005-0097181 | 10/2005 |
| KR | 10-0601981 | 7/2006 |
| KR | 10-2010-0002803 | 1/2010 |

OTHER PUBLICATIONS

Internatnional Search Report dated Sep. 25, 2012 in corresponding International Patent Application No. PCT/KR2012/001119 (3 pages, in Korean).
(Continued)

*Primary Examiner* — Mohamed Charioui
*Assistant Examiner* — Jeremy Delozier
(74) *Attorney, Agent, or Firm* — NSIP Law

(57) ABSTRACT

A motion of a model including a joint, at least one body part that rotates with respect to the joint, and a plurality of inertial sensors attached to each body part and measuring a rotational motion of the body part is tracked by obtaining a rotational matrix of a sensor coordinate system fixed to each of the inertial sensors with respect to an inertial coordinate system fixed to ground, by using a signal measured by the inertial sensor attached to each body part; obtaining a rotational matrix of the sensor coordinate systems with respect to a body part coordinate system fixed to each body part, by using an obtained rotational matrix value of the (Continued)

sensor coordinate system; obtaining a rotational matrix of each body part coordinate system with respect to the inertial coordinate system, by using a calculated rotational matrix of the sensor coordinate systems; and calculating a joint variable with respect to each body part, by using a calculated rotational matrix of the body part coordinate system.

4 Claims, 4 Drawing Sheets

(51) Int. Cl.
*A61B 5/11* (2006.01)
*A61B 5/00* (2006.01)
(52) U.S. Cl.
CPC .......... *A61B 5/6823* (2013.01); *A61B 5/6824* (2013.01); *A61B 5/6825* (2013.01); *A61B 5/6828* (2013.01); *A61B 5/6829* (2013.01); *A61B 5/6831* (2013.01); *A61B 2503/10* (2013.01); *A61B 2505/09* (2013.01)

(56) References Cited

OTHER PUBLICATIONS

Korean Office Action dated Nov. 19, 2012 on corresponding Korean Patent Application No. KR10-2011-0049804 (7 pages, in Korean including English Translation).

\* cited by examiner

METHOD OF MOTION TRACKING

CROSS-REFERENCE TO RELEATED APPLICATIONS

This application is a National Phase entry of PCT Application No. PCT/KR2012/001119, filed on Feb. 15, 2012, which claims priority under 35 U.S. C. §119(e), 120 and 365(c) to Korean Patent Application No. 10-2011-0049804, filed on May 25, 2011, the entire disclosure of which is incorporated herein by refernce for all purposes.

TECHNICAL FIELD

The present invention relates to a motion tracking method, and more particularly, to a motion tracking method which can accurately track a motion even when an inertial measurement unit (IMU) is attached to a human body in any directions because there is no need to accurately match the direction of a sensor coordinate system of each IMU with the direction of a body part coordinate system.

BACKGROUND ART

Motion tracking or motion capture is a method of tracking a motion of a human body and is technology used for various fields such as film or animation production, sports motion analysis, medical rehabilitation, etc.

As a motion tracking method, there is an optical method and a magnetic field method. In the optical method, a reflection marker is attached to a human body and an infrared ray is irradiated onto the reflection marker by using an infrared camera so as to receive a light reflected from the reflection marker. Also, in the magnetic field method, a magnetic member is attached to the body of a user and when the user moves in a field where a magnetic field is formed, a motion of the magnetic member is determined by a change in the magnetic field. Recently, since a sensor is made small and light due to the development of micro-electromechanical systems (MEMS) technology, a method of using an inertial measurement unit (IMU) has been introduced. The IMU is an apparatus for measuring an inertial force acting on an object moved by an applied acceleration. By measuring translational inertia, rotational inertia, terrestrial magnetism, etc. of an object to be measured, various motion information such as acceleration, speed, direction, distance, etc. of the object may be provided.

FIG. 1 illustrates a state in which a plurality of inertial sensors S are attached to a human body which has joints and body parts. FIG. 2 is a view schematically illustrating a kinematical model of the human body illustrated in FIG. 1. FIG. 3 is a view for explaining coordinate systems used for the kinematical model of FIG. 2. As illustrated in FIG. 2, a human body may be represented as a kinematical model having joints J1, J2, and J3 and body parts 1, 2, 3, and 4 that are rotatable with respect to the joints J1, J2, and J3. The inertial sensors S1, S2, S3, and S4 are not attached to the joints J1, J2, and J3, but to the body parts 1, 2, 3, and 4 such as the trunk, an upper arm, a lower arm, and the pelvis, respectively.

Thus, information regarding a motion of a human body may be obtained by using the inertial sensors S1, S2, S3, and S4 attached to the body parts 1, 2, 3, and 4. A motion of a human body may be tracked by processing the information.

However, when the inertial sensors S1, S2, S3, and S4 are attached to the body parts 1, 2, 3, and 4, as illustrated in FIG. 3, the directions of coordinate systems {A and B} fixed to each of the body parts 1, 2, 3, and 4 need to be accurately matched with the directions of coordinate systems $\{S_A$ and $S_B\}$ of each of the inertial sensors S1, S2, S3, and S4. However, since the surface of a human body is uneven, it is practically almost impossible to match the directions of the coordinate systems. Thus, when a motion is to be tracked by using the inertial sensors S, there is a need to match the directions of the coordinate systems.

DISCLOSURE

Technical Problem

Since the surface of a human body is uneven, it is practically almost impossible to match the directions of the coordinate systems. Thus, when a motion is to be tracked by using the inertial sensors S, there is a need to match the directions of the coordinate systems.

Technical Solution

According to an aspect of the present invention, a method of tracking a motion of a model including a joint, at least one body part that rotates with respect to the joint, and a plurality of inertial sensors attached to each body part and measuring a rotational motion of the body part includes a sensor posture measurement operation of obtaining a rotational matrix of a sensor coordinate system fixed to each of the plurality of inertial sensors with respect to an inertial coordinate system fixed to ground, by using a signal measured by the inertial sensor attached to each body part; a rotational matrix conversion operation of obtaining a rotational matrix of the sensor coordinate systems with respect to a body part coordinate system fixed to each body part, by using a rotational matrix value of the sensor coordinate system obtained in the sensor posture measurement operation; a body part posture calculation operation of obtaining a rotational matrix of each body part coordinate system with respect to the inertial coordinate system, by using a rotational matrix of the sensor coordinate systems calculated in the rotational matrix conversion operation; and a joint variable calculation operation of calculating a joint variable with respect to each body part, by using a rotational matrix of the body part coordinate system calculated in the body part posture calculation operation.

Advantageous Effects

According to the present invention, since the rotational matrix conversion operation of obtaining a rotational matrix of the sensor coordinate systems with respect to the body part coordinate systems fixed to the body parts, respectively, by using the rotational matrix of the sensor coordinate systems obtained in the sensor posture measurement operation is provided, there is no need to accurately match the direction of the body part coordinate system with the direction of the sensor coordinate system of each of the inertial sensor. Thus, accurate motion tracking may be possible even when the inertial sensors are attached to a human body in any directions.

DESCRIPTION OF DRAWINGS

The above and other features and advantages of the present invention will become more apparent by describing in detail exemplary embodiments thereof with reference to the attached drawings in which.

BEST MODE

Figure 1:
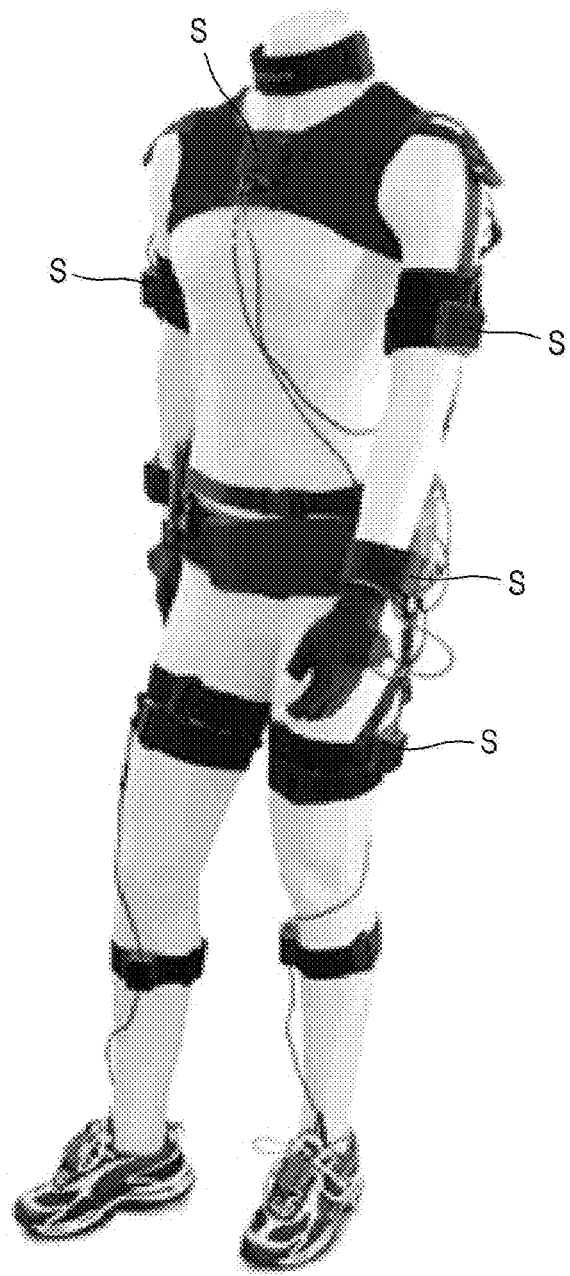
FIG. 1 is an image illustrating a state in which a plurality of inertial sensors are attached to a human body which has joints and body parts.

According to an aspect of the present invention, a method of tracking a motion of a model including a joint, at least one body part that rotates with respect to the joint, and a plurality of inertial sensors attached to each body part and measuring a rotational motion of the body part includes a sensor posture measurement operation of obtaining a rotational matrix of a sensor coordinate system fixed to each of the plurality of inertial sensors with respect to an inertial coordinate system fixed to ground, by using a signal measured by the inertial sensor attached to each body part; a rotational matrix conversion operation of obtaining a rotational matrix of the sensor coordinate systems with respect to a body part coordinate system fixed to each body part, by using a rotational matrix value of the sensor coordinate system obtained in the sensor posture measurement operation; a body part posture calculation operation of obtaining a rotational matrix of each body part coordinate system with respect to the inertial coordinate system, by using a rotational matrix of the sensor coordinate systems calculated in the rotational matrix conversion operation; and a joint variable calculation operation of calculating a joint variable with respect to each body part, by using a rotational matrix of the body part coordinate system calculated in the body part posture calculation operation.

The model may be a human body including a trunk, a pelvis coupled to the trunk through a joint, an upper arm coupled to the trunk through a joint, and a lower arm coupled to the upper arm through a joint.

The inertial sensor may be a sensor capable of measuring translational inertia, rotational inertia, and terrestrial magnetism.

The inertial sensor may transmit a measured signal to the outside wirelessly.

The inertial sensor may be manufactured according to micro-electromechanical systems (MEMS) technology to be small and light.

MODE FOR INVENTION

The attached drawings for illustrating exemplary embodiments of the present invention are referred to in order to gain a sufficient understanding of the present invention, the merits thereof, and the objectives accomplished by the implementation of the present invention. Hereinafter, the present invention will be described in detail by explaining exemplary embodiments of the invention with reference to the attached drawings. Like reference numerals in the drawings denote like elements.

As used herein, the term "and/or" includes any and all combinations of one or more of the associated listed items. Expressions such as "at least one of," when preceding a list of elements, modify the entire list of elements and do not modify the individual elements of the list.

Figure 4:
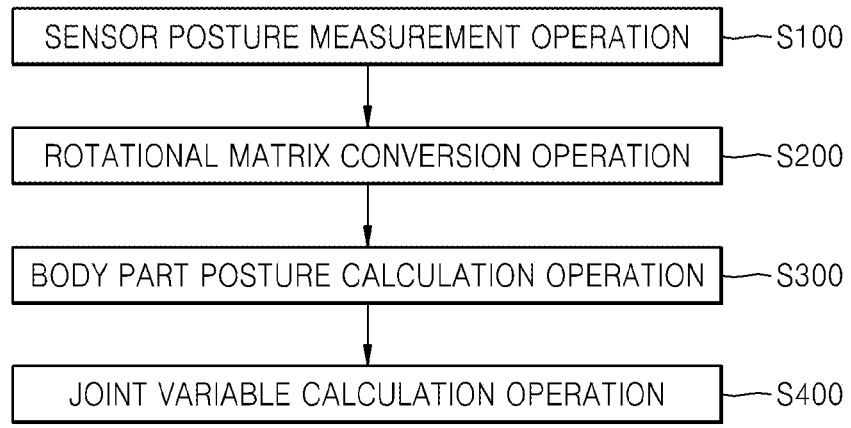
FIG. 4 is a flowchart for explaining a motion tracking method according to an embodiment of the present invention.
Figure 5:
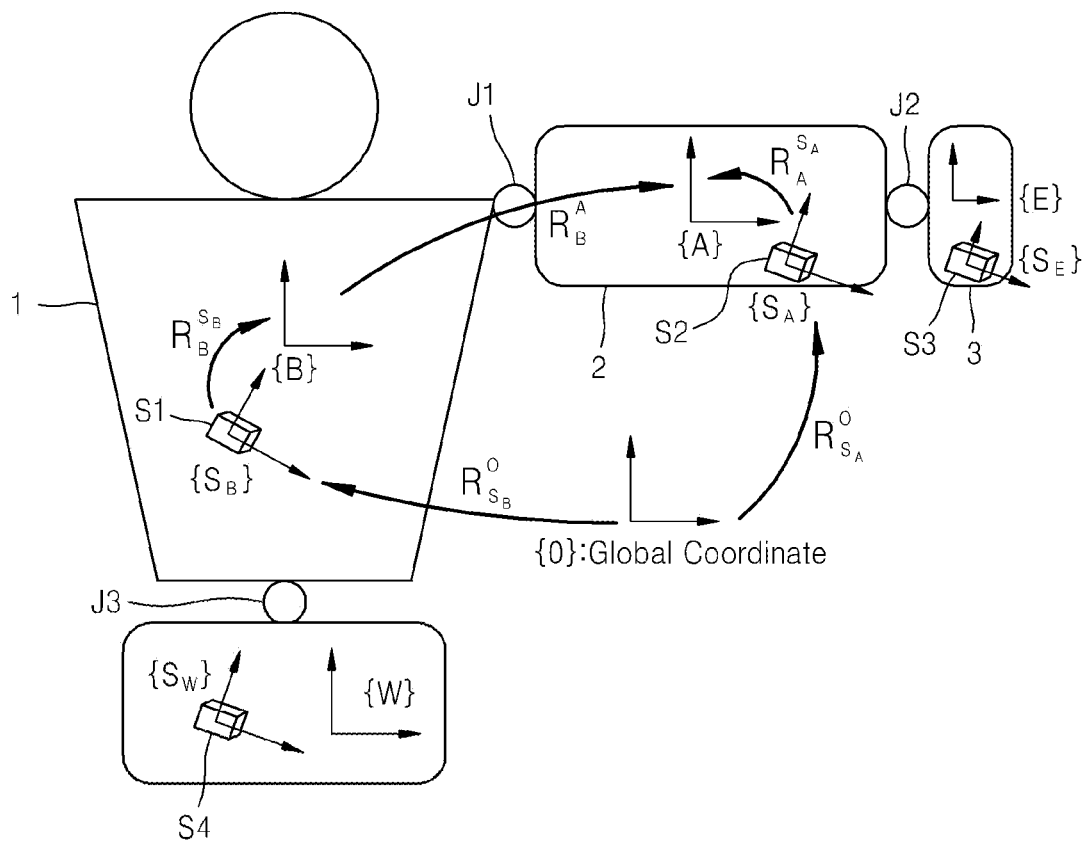
FIG. 5 is a view for explaining necessary coordinate systems used for the motion tracking method of FIG. 4 and a rotational matrix among the coordinate systems.

FIG. 4 is a flowchart for explaining a motion tracking method according to an embodiment of the present invention. FIG. 5 is a view for explaining necessary coordinate systems used for the motion tracking method of FIG. 4 and a rotational matrix among the coordinate systems.

Referring to FIGS. 4 and 5, the motion tracking method according to the present embodiment is a method of tracking a motion of a human body by attaching a plurality of inertial sensors S to a dynamic model formed of joints and body parts, for example, a moving object such as a human body. The motion tracking method according to the present embodiment includes a sensor posture measurement operation S100, a rotational matrix conversion operation S200, a body part posture calculation operation S300, and a joint variable calculation operation S400.

Before explaining the motion tracking method, a human body model used for explaining a process of adopting the motion tracking method according to the present embodiment will be first described.

Figure 2:
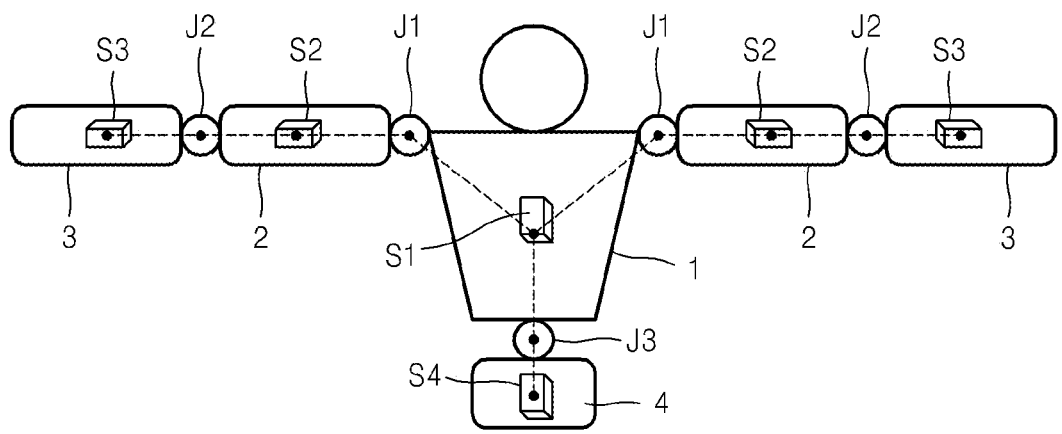
FIG. 2 is a view schematically illustrating a kinematical model of the human body illustrated in FIG. 1.
Figure 3:
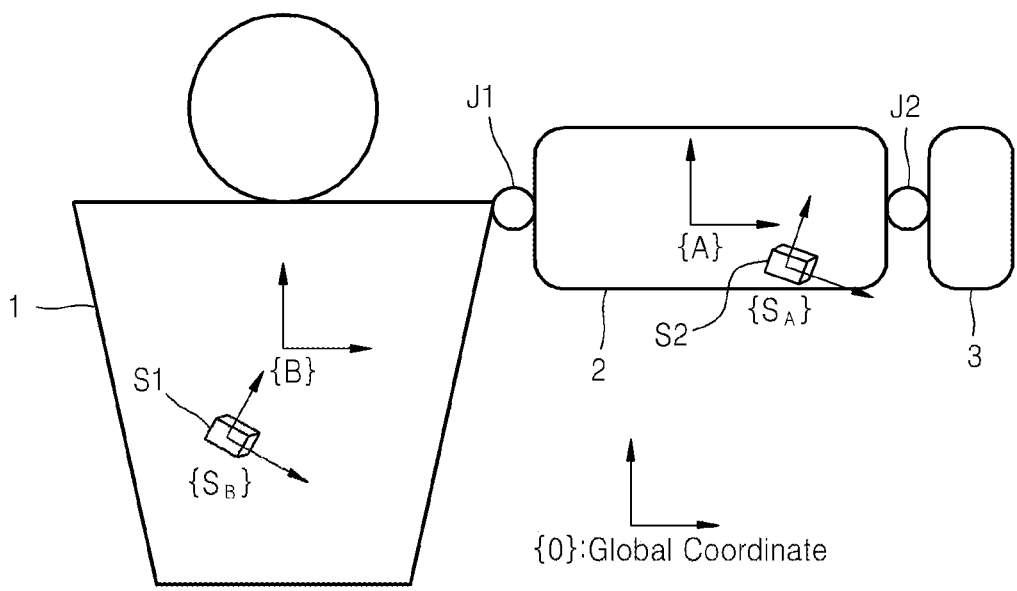
FIG. 3 is a view for explaining coordinate systems used for the kinematical model of FIG. 2.

The human body model, as illustrated in FIG. 2, includes the joints J1, J2, and J3, at least one of the body parts 1, 2, 3, and 4 that rotates with respect to at least one of the joints J1, J2, and J3, and the inertial sensors S1, S2, S3, and S4 attached to the body parts 1, 2, 3, and 4 and measuring rotational motions of the body parts 1, 2, 3, and 4, respectively. In the present embodiment, the inertial sensors S1, S2, S3, and S4 are sensors manufactured according to MEMS technology and may each be inertial measurement units (IMU) capable of measuring translational inertia, rotational inertia, and terrestrial magnetism. A measured signal may be transmitted to the outside wirelessly.

In detail, the human body model, as illustrated in FIG. 2, includes the trunk 1, the pelvis 4 coupled to the trunk 1 through the waist joint J3, the upper arm 2 coupled to the trunk 1 through the shoulder joint J1, and the lower arm 3 coupled to the upper arm 2 through an elbow joint J2. Accordingly, the trunk 1, the upper arm 2, the lower arm 3, and the pelvis 4 form the body parts 1, 2, 3, and 4 of the human body model, respectively. The waist joint J3 between the trunk 1 and the pelvis 4 has a joint variable Q3 of three degrees of freedom. The shoulder joint J1 between the upper arm 2 and the trunk 1 has a joint variable Q1 of three degrees of freedom. The elbow joint J2 between the lower arm 3 and the upper arm 2 has a joint variable Q2 of three degrees of freedom. The joint variables Q1, Q2, and Q3 denote a rotational motion of each of the joints J1, J2, and J3 and are well known to one skilled in the art so that detailed descriptions thereof are omitted herein.

In the present embodiment, a variety of coordinate systems are used. As illustrated in FIG. 5, there are an global coordinate system {0} that is fixed to the ground as a inertial coordinate system, sensor coordinate systems {$S_B$, $S_A$, $S_E$, and $S_W$} that are fixed to the inertial sensors S1, S2, S3, and S4, respectively, and body part coordinate systems {B, A, E, and W} that are fixed to the body parts 1, 2, 3, and 4, respectively.

An example of applying the motion tracking method to the above-described human body model will now be described.

First, as the body parts 1, 2, 3, and 4 perform rotational motions, signals measured by the inertial sensors S1, S2, S3, and S4 attached to the body parts 1, 2, 3, and 4, respectively, are wirelessly transmitted to the outside. A rotational matrix $R^0_{SB}$, $R^0_{SA}$, $R^0_{SE}$, and $R^0_{SW}$ of the sensor coordinate systems $\{S_B, S_A, S_E, \text{and } S_W\}$ fixed to the inertial sensors S1, S2, S3, and S4, respectively, is obtained with respect to the global coordinate system $\{0\}$ by using the measured signals. (Sensor posture measurement operation S100)

Next, a rotational matrix $R_B^{SB}$, $R_A^{SA}$, $R_E^{SE}$, and $R_W^{SW}$ of the sensor coordinate systems $\{S_B, S_A, S_E, \text{and } S_W\}$ is obtained with respect to the body part coordinate systems $\{B, A, E, \text{and } W\}$ fixed to the body parts 1, 2, 3, and 4, respectively, by using the rotational matrix $R^0_{SB}$, $R^0_{SA}$, $R^0_{SE}$, and $R^0_{SW}$ of the sensor coordinate systems $\{S_B, S_A, S_E, \text{and } S_W\}$ obtained in the sensor posture measurement operation S100.

Equation (1), derived from an equation of a motion between the trunk 1 and the upper arm 2, is used. Here, $R_A^B$ denotes a rotational matrix between the body part coordinate system $\{B\}$ fixed to the trunk 1 and the body part coordinate system $\{A\}$ fixed to the upper arm 2.

$$R^0_{SA} R_A^{SA} = R^0_{SB} R_B^{SB} R_A^B \quad (1)$$

Since the unknowns in Equation (1) are $R_A^{SA}$ and $R_B^{SB}$, the other variables $R^0_{SA}$, $R^0_{SB}$, and $R_A^B$ are constants in order to obtain the unknowns $R_A^{SA}$, and $R_B^{SB}$. In the present embodiment, the other variables $R^0_{SA}$, $R^0_{SB}$, and $R_A^B$ are determined after a human body model performs three predetermined motions. The three motions may be, for example, a motion of stretching an arm forward, a motion of raising an arm upwards, and a motion of stretching an arm laterally. When Equation (1) is applied to the three motions, the following Equation (2) is produced. Here, $R^0_{SA}(k)$, $R^0_{SB}(k)$, and $R_A^B(k)$ are constant values determined to the three motions.

$$R^0_{SA}(k) R_A^{SA} = R^0_{SB}(k) R_B^{SB} R_A^B(k), \text{ where } k=1,2, \text{ and } 3 \quad (1)$$

Likewise, by applying an equation similar to Equation (2) to the trunk 1 and the pelvis 4 and an equation similar to Equation (2) to the trunk 1 and the lower arm 3, the rotational matrix $R_B^{SB}$, $R_A^{SA}$, $R_E^{SE}$, and $R_W^{SW}$ of the sensor coordinate systems $\{S_B, S_A, S_E, \text{and } S_W\}$ is obtained with respect to the body part coordinate systems $\{B, A, E, \text{and } W\}$. (Rotational matrix conversion operation S200)

Figure 6:
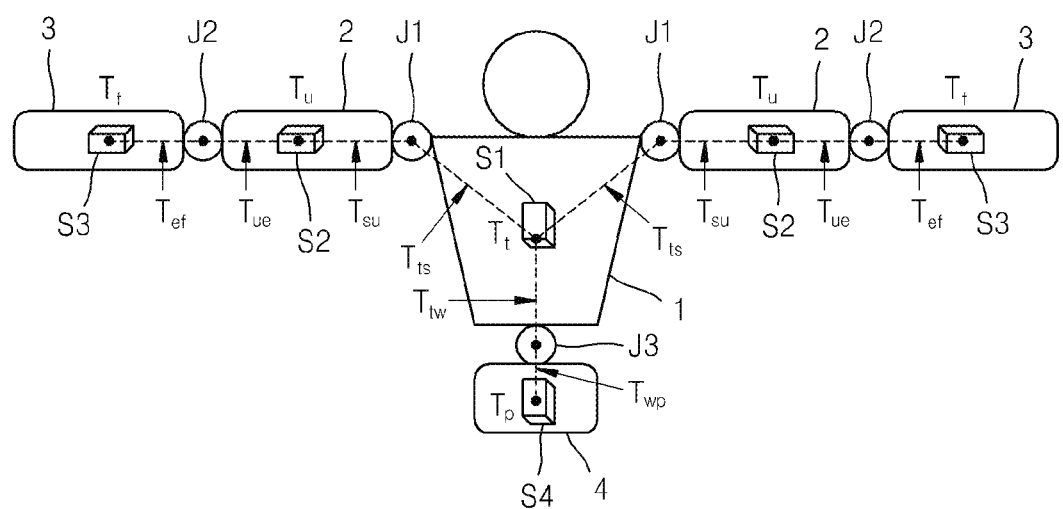
FIG. 6 is a view for explaining necessary rotational matrix for the motion tracking method of FIG. 4.

Next, by using the rotational matrix $R_B^{SB}$, $R_A^{SA}$, $R_E^{SE}$, and $R_W^{SW}$ of the sensor coordinate systems $\{S_B, S_A, S_E, \text{and } S_W\}$ calculated in the rotational matrix conversion operation S200, a rotational matrix $R_B^0$, $R_A^0$, $R_E^0$, and $R_W^0$ of each of the body part coordinate systems $\{B, A, E, \text{and } W\}$ is obtained with respect to the global coordinate system $\{0\}$. In the following description, the rotational matrix $R_B^0$, $R_A^0$, $R_E^0$, and $R_W^0$ of the body part coordinate systems $\{B, A, E, \text{and } W\}$ is expressed by a rotational matrix $\{T_t, T_u, T_f, T_p\}$ as illustrated in FIG. 6. Here, the following Equations (3) through (6) are used therefor.

$$T_t = R_B^0 = R^0_{SB} R_B^{SB} \quad (3)$$

$$T_u = R_A^0 = R^0_{SA} R_A^{SA} = R^0_{SB} R_B^{SB} R_A^B \quad (4)$$

$$T_f = R_E^0 = R^0_{SE} R_E^{SE} = R^0_{SB} R_B^{SB} R_A^B R_E^A \quad (5)$$

$$T_p = R_W^0 = R^0_{SW} R_W^{SW} = R^0_{SB} R_B^{SB} R_W^B \quad (6)$$

Here, $R_E^A$ denotes a rotational matrix between the body part coordinate system $\{A\}$ fixed to the upper arm 2 and the body part coordinate system $\{E\}$ fixed to the lower arm 3. $R_W^B$ denotes a rotational matrix between the body part coordinate system $\{B\}$ fixed to the trunk 1 and the body part coordinate system $\{W\}$ fixed to the pelvis 4. (Body part posture calculation operation S300)

Finally, by using the rotational matrix $\{T_t, T_u, T_f, T_p\}$ of the body part coordinate systems $\{B, A, E, \text{and } W\}$ calculated in the body part posture calculation operation S300, the joint variables Q1, Q2, and Q3 are calculated with respect to the joints J1, J2, and J3, respectively. The following Equation (7) is derived from the kinematics from the trunk 1 to the upper arm 2, the following Equation (8) is derived from the kinematics from the upper arm 2 to the lower arm 3, and the following Equation (9) is derived from the kinematics from the trunk 1 to the pelvis 4.

$$T_t = T_u T_{su} e^{Q1} T_{ts} \quad (7)$$

$$T_u = T_f T_{ef} e^{Q2} T_{ue} \quad (8)$$

$$T_t = T_p T_{wp} e^{Q3} T_{tw} \quad (9)$$

Here, $T_{ts}$ denotes a matrix in consideration of a distance from the trunk 1 to the shoulder joint J1. $T_{su}$ denotes a matrix in consideration of a distance from the shoulder joint J1 to the upper arm 2. $T_{ue}$ denotes a matrix in consideration of a distance from the upper arm 2 to the elbow joint J2. $T_{ef}$ denotes a matrix in consideration of a distance from the shoulder joint J1 to the lower arm 3. $T_{tw}$ denotes a matrix in consideration of a distance from the trunk 1 to the waist joint J3. $T_{wp}$ denotes a matrix in consideration of a distance from the waist joint J3 to the pelvis 4.

To summarize Equations (7) through (9), the following Equations (10) through (12) are derived, $$Q1 = \log((T_u T_{su})^{-1} T_t T_{ts}^{-1}) \quad (10)$$

$$Q2 = \log((T_f T_{ef})^{-1} T_u T_{ue}^{-1}) \quad (11)$$

$$Q3 = \log((T_p T_{wp})^{-1} T_t T_{tw}^{-1}) \quad (12)$$

The joint variables Q1, Q2, and Q3 of the joints J1, J2, and J3 may be obtained from the Equations (10) through (12). (Joint variable calculation operation S400)

In the above-described motion tracking method, since the rotational matrix conversion operation S200 for obtaining the rotational matrix $R_B^{SB}$, $R_A^{SA}$, $R_E^{SE}$, and $R_W^{SW}$ of the sensor coordinate systems $\{S_B, S_A, S_E, \text{and } S_W\}$ with respect to the body part coordinate systems $\{B, A, E, \text{and } W\}$ respectively fixed to the body parts 1, 2, 3, and 4, by using the rotational matrix $R^0_{SB}$, $R^0_{SA}$, $R^0_{SE}$, and $R^0_{SW}$ of the sensor coordinate systems $\{S_B, S_A, S_E, \text{and } S_W\}$ obtained in the sensor posture measurement operation S100 is provided, there is no need to accurately match the directions of the body part coordinate systems $\{B, A, E, \text{and } W\}$ fixed to the body parts 1, 2, 3, and 4, respectively, with the directions of the sensor coordinate systems $\{S_B, S_A, S_E, \text{and } S_W\}$ of the inertial sensors S1, S2, S3, and S4. Thus, accurate motion tracking may be possible even when the inertial sensors S1, S2, S3, and S4 are attached to a human body in any directions.

Also, in the motion tracking method, since the joint variable calculation operation S400 for calculating the joint variables Q1, Q2, and Q3 with respect to each of the joints J1, J2, and J3, by using the rotational matrix $\{T_t, T_u, T_f, T_p\}$ of the body part coordinate systems $\{B, A, E, \text{and } W\}$ calculated in the body part posture calculation operation S300 is provided, the joint variables Q1, Q2, and Q3 may be obtained by using the rotational matrix $\{T_t, T_u, T_f, T_p\}$ of the joints J1, J2, and J3.

Also, in the motion tracking method, since the inertial sensors S1, S2, S3, and S4 for measuring translational inertia, rotational inertia, and terrestrial magnetism are used, compared to a conventional optical method or a magnetic field method, response speeds of the inertial sensors S1, S2, S3, and S4 for measuring rotational motions of the body parts 1, 2, 3, and 4 are fast. Accordingly, even when a human body model moves fast, accurate motion tracking is possible.

In addition, in the motion tracking method, since the inertial sensors S1, S2, S3, and S4 capable of transmitting measured signals to the outside wirelessly are used, it is easy to attach the inertial sensors S1, S2, S3, and S4 to a human body and complicated wiring is not needed so that a motion of a human body, which is an object of motion tracking, may be tracked without hindrance.

In the motion tracking method, since the inertial sensors S1, S2, S3, and S4 are manufactured according to MEMS technology to be small and light, the inertial sensors S1, S2, S3, and S4 are easy to carry and provide comfort like they are not attached to a human body.

In the present embodiment, although motion tracking is performed with respect to a human body model, mainly to the upper body including the trunk 1, the pelvis 4 coupled to the trunk 1, the upper arm 2 coupled to the trunk 1, and the lower arm 3 coupled to the upper arm 2, the motion tracking may also be applied to a human body model including the lower body such as thigh, calf, foot, etc.

As described above, according to the present invention, since the rotational matrix conversion operation of obtaining a rotational matrix of the sensor coordinate systems with respect to the body part coordinate systems fixed to the body parts, respectively, by using the rotational matrix of the sensor coordinate systems obtained in the sensor posture measurement operation is provided, there is no need to accurately match the direction of the body part coordinate system with the direction of the sensor coordinate system of each of the inertial sensor. Thus, accurate motion tracking may be possible even when the inertial sensors are attached to a human body in any directions.

While this invention has been particularly shown and described with reference to exemplary embodiments thereof, it will be understood by those skilled in the art that various changes in form and details may be made therein without departing from the spirit and scope of the invention as defined by the appended claims.

The invention claimed is:

1. A method of tracking a motion of a model comprising a joint, body parts that rotate with respect to the joint, and inertial sensors attached to each of the body parts to measure a rotational motion of each of the body parts, the method comprising:

attaching the inertial sensors to each of the body parts in different orientations with respect to one or more of each of the body parts and ground, wherein the inertial sensors are attached to each of the body parts without matching a direction of the body part coordinate system with a corresponding direction of the sensor coordinate system of each of the inertial sensors;

tracking motion of the body parts using the inertial sensors;

capturing a motion of the body parts using a joint variable and a rotational matrix of the body part coordinate system;

outputting the calculated joint variable as a captured motion of the body parts;

a sensor posture measurement operation of obtaining the rotational matrix of the sensor coordinate system fixed to each of the inertial sensors with respect to an inertial coordinate system fixed to the ground using a signal measured by the inertial sensors;

a rotational matrix conversion operation of obtaining the rotational matrix of the sensor coordinate systems with respect to the body part coordinate system fixed to each of the body parts, using a rotational matrix value of the sensor coordinate system obtained in the sensor posture measurement operation;

a body part posture calculation operation of obtaining a rotational matrix of each body part coordinate system with respect to the inertial coordinate system using a rotational matrix of the sensor coordinate systems calculated in the rotational matrix conversion operation;

using a rotational matrix value of the sensor coordinate system obtained in the obtaining of the rotation matrix of the sensor coordinate system fixed to each of the inertial sensors with respect to the inertial coordinate system fixed to the ground, and a signal measured by the inertial sensor attached to each of the body parts, as each of the body parts performs three or more motions; and a joint variable calculation operation of calculating a joint variable with respect to each body part, using a rotational matrix of the body part coordinate system calculated in the body part posture calculation operation, wherein the obtaining of the rotational matrix of the sensor coordinate systems with respect to the body part coordinate system fixed to each of the body parts comprises using a signal measured by the inertial sensor attached to each of the body parts as each of the body parts performs three or more motions, wherein the calculating of the joint variable further comprises transforming motion data, measured by the inertial sensor with respect to the sensor coordinate system fixed to each of the inertial sensors, using the rotational matrix of the body part coordinate system to produce the calculated joint variable, and wherein the model is a human body comprising a trunk, a pelvis coupled to the trunk through a joint, an upper arm coupled to the trunk through a joint, and a lower arm coupled to the upper arm through a joint, a waist joint between the trunk and the pelvis comprising a joint variable of three degrees of freedom, a shoulder joint between the upper arm and the trunk comprising a joint variable of three degrees of freedom, and an elbow joint between the lower arm and the upper arm comprising a joint variable of three degrees of freedom.

2. The method of claim 1, wherein the inertial sensor is capable of measuring translational inertia, rotational inertia, and terrestrial magnetism.

3. The method of claim 1, wherein the inertial sensor is configured to wirelessly transmit a measured signal.

4. The method of claim 1, wherein the inertial sensor is manufactured according to micro-electromechanical systems (MEMS) technology.

* * * * *